(12) United States Patent
Fousse et al.

(10) Patent No.: US 12,318,471 B2
(45) Date of Patent: Jun. 3, 2025

(54) COSMETIC CARE METHOD BASED ON PHOTOACTIVE EXTRACTS OF MICROALGAE

(71) Applicants: LABORATOIRES D'ANJOU, Paris (FR); GREENSEA, Saint-Beauzire (FR)

(72) Inventors: Carole Fousse, Paris (FR); Jean-Paul Cadoret, Meze (FR)

(73) Assignees: LABORATOIRES D'ANJOU, Paris (FR); GREENSEA, Saint-Beauzire (FR)

( * ) Notice: Subject to any disclaimer, the term of this patent is extended or adjusted under 35 U.S.C. 154(b) by 661 days.

(21) Appl. No.: 17/608,234

(22) PCT Filed: May 4, 2020

(86) PCT No.: PCT/FR2020/000159
§ 371 (c)(1),
(2) Date: Nov. 2, 2021

(87) PCT Pub. No.: WO2020/221971
PCT Pub. Date: Nov. 5, 2020

(65) Prior Publication Data
US 2022/0249355 A1    Aug. 11, 2022

(30) Foreign Application Priority Data
May 2, 2019   (FR) ...................................... 1904608

(51) Int. Cl.
*A61K 36/00*     (2006.01)
*A61K 8/9722*   (2017.01)
*A61Q 19/08*     (2006.01)

(52) U.S. Cl.
CPC ............ *A61K 8/9722* (2017.08); *A61Q 19/08* (2013.01); *A61K 2800/81* (2013.01); *A61K 2800/88* (2013.01)

(58) Field of Classification Search
None
See application file for complete search history.

(56) References Cited

U.S. PATENT DOCUMENTS

2006/0241726 A1* 10/2006 Whitehurst ............. A61P 17/00
607/86

FOREIGN PATENT DOCUMENTS

| FR | 2858771 A1 | 2/2005 |
|----|------------|--------|
| FR | 2894473 A1 | 6/2007 |
| FR | 2917299 A1 | 12/2008 |
| FR | 2948876 A1 | 2/2011 |
| FR | 2980698 A1 | 4/2013 |
| KR | 20110044494 A | 4/2011 |

OTHER PUBLICATIONS

Jo et al. (2012) Toxicol. Res. vol. 28, No. 4., pp. 241-248. (Year: 2012).*
International Search Report and English translation for corresponding international application No. PCT/FR2020/000159, dated Jul. 13, 2020.

* cited by examiner

*Primary Examiner* — Russell G Fiebig
(74) *Attorney, Agent, or Firm* — LEASON ELLIS LLP

(57) ABSTRACT

The present invention concerns a cosmetic care method for the skin comprising the steps of applying, to the skin, a cosmetic composition comprising photoactive extracts of at least one microalgae, and exposing the area to which the composition has been applied to light. The invention also comprises a device for cosmetic care according to the method, and a kit comprising a cosmetic composition comprising photoactive extracts of at least one microalgae and a lighting device according to the invention. The invention finally comprises the use of the device according to the invention for an anti-aging and/or anti-wrinkle treatment and/or a treatment promoting the healing of the skin area.

4 Claims, 5 Drawing Sheets

Fig.3A

Figure 1:
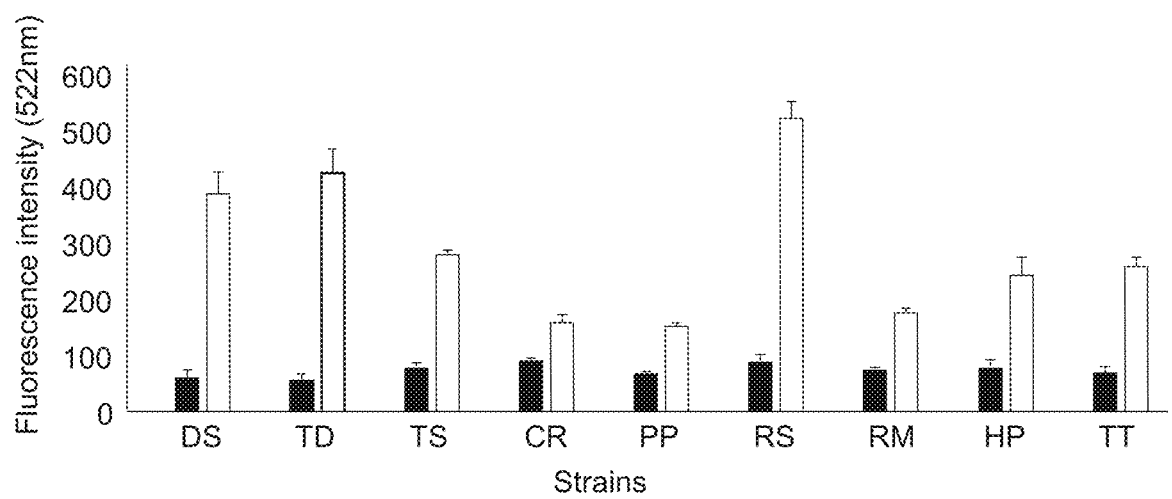

| Gene | Official Full Name | Activity |
|---|---|---|
| AQP1 | Aquaporin 1 | Detoxification - hydration |
| AQP3 | Aquaporin 3 | Detoxification - hydration |
| ATP5A1 | ATP synthase, H+ transporting, mitochrondrial F1 complex, alpha subunit 1 | Energetic metabolism |
| AZGP1 | Alpha-2-glycoprotein 1, zinc-binding | Pigmentation |
| BAX | BCL2-associated X protein | Apoptosis |
| BCL2 | B-cell CLL/lymphoma 2 | Apoptosis |
| BGN | Biglycan | Extra-cellular matrix |
| BSG | Basigin | Longevity |
| CAMP | Cathelicidin antimicrobial peptide | Antimicrobial – anti-inflammatory |
| CAT | Catalase | Antioxidant |
| CD36 | CD36 molecule | Adhesion |
| CD44 | CD44 molecule | Adhesion |
| CDC42 | Cell division cycle 42 | Adhesion |
| CLDN1 | Claudin 1 | Cohesion |
| COL17A1 | Collagen, type XVII, alpha 1 | Adhesion – basement membrane |
| COL1A1 | Collagen, type I, alpha 1 | Extra-cellular matrix |
| COL3A1 | Collagen, type III, alpha 1 | Extra-cellular matrix |
| COL4A1 | Collagen, type IV, alpha 1 | Adhesion – basement membrane |
| COL5A1 | Collagen, type V, alpha 1 | Extra-cellular matrix |
| COL7A1 | Collagen, type VII, alpha 1 | Adhesion – basement membrane |
| COX2 | Prostaglandin-Endoperoxide Synthase 2 (COX2) | Inflammation |
| CTNNA1 | Catenin (cadherin-associated protein), alpha 1 | Adhesion |
| DCN | Decorin | Extra-cellular matrix |
| DKK1 | Dickkopf homolog 1 | Pigmentation |
| DPT | Dermatopontin | Extra-cellular matrix – structure |
| EGF | Epidermal growth factor | Renewal |
| ELN | Elastin | Extra-cellular matrix |
| EPPK1 | Epiplakin 1 | Cohesion |
| EVPL | Envoplakin | Cohesion |
| FBN1 | Fibrillin 1 | Extra-cellular matrix |
| FBN2 | Fibrillin 2 | Extra-cellular matrix |
| FLG | Filaggrin (new current marker) | Epidermal differentiation |
| FN1 | Fibronectin 1 | Adhesion |
| FST | Follistatin | Inflammation |
| GLRX | Glutaredoxin | Antioxidant |
| GPX1 | Glutathione peroxidase 1 | Antioxidant |
| GSS | Glutathione synthetase | Pigmentation |
| HAS2 | Hyaluronan synthase 2 | Extra-cellular matrix |
| HBEGF | Heparin-binding EGF-like growth factor | Renewal |

Fig.3B

| HMOX1 | Heme oxygenase 1 | Antioxidant |
|---|---|---|
| IGFBP6 | Insulin-like growth factor binding protein 6 | Longevity |
| IL1A | Interleukin 1, alpha | Inflammation |
| IL6 | Interleukin 6 | Inflammation |
| IL8 | Interleukin 8 | Inflammation |
| INSR | Insulin receptor | Longevity |
| ITGA2 | Integrin, alpha 2 | Adhesion |
| IVL | Involucrin | Epidermal differentiation |
| LAMA5 | Laminin, alpha 5 | Adhesion |
| LAMC2 | Laminin, gamma 2 | Adhesion |
| LOR | Loricrin | Epidermal differentiation |
| LOX | Lysyl oxidase | Extra-cellular matrix - structure |
| LOXL1 | Lysyl oxidase-like 1 | Extra-cellular matrix – structure |
| LUM | Lumican | Extra-cellular matrix – structure |
| MGST1 | Microsomal glutathione S-transferase 1 | Antioxidant |
| MMP1 | Matrix metallopeptidase 1 | Extra-cellular matrix – degradation |
| MMP3 | Matrix metallopeptidase 3 | Extra-cellular matrix – degradation |
| MMP9 | Matrix metallopeptidase 9 | Extra-cellular matrix – degradation |
| MSRA | Methionine sulfoxide reductase A | Antioxidant |
| MSRB2 | Methionine sulfoxide reductase B2 | Antioxidant |
| NRF2 | NFE2 related factor 2 (NFE2L2) | Antioxidant |
| OCLN | Occludin | Cohesion |
| P4HA1 | Prolyl 4-hydroxylase, alpha polypeptide 1 | Extra-cellular matrix – structure |
| PI3 | Peptidase inhibitor 3, skin-derived | Extra-cellular matrix – protection |
| PLOD3 | Procollagen-lysine, 2-oxoglutarate 5-dioxygenase 3 | Extra-cellular matrix – structure |
| POMC | Proopiomelanocortin | Pigmentation |
| PPIA | Peptidylprolyl isomerase A | Anti-apoptotic antioxidant |
| PRDX1 | Peroxiredoxin 1 | Antioxidant |
| PXN | Paxillin | Adhesion |
| S100A7 | S100 calcium binding protein A7 (Psoriasine) | Inflammation |
| SDC1 | Syndecan 1 | Cohesion |
| SDC4 | Syndecan 4 | Extra-cellular matrix |
| SIRT1 | Sirtuin 1 | Longevity |
| SIRT2 | Sirtuin 2 | Longevity |
| SIRT3 | Sirtuin 3 | Longevity |
| SIRT4 | Sirtuin 4 | Longevity |
| SIRT5 | Sirtuin 5 | Longevity |
| SIRT6 | Sirtuin 6 | Longevity |
| SIRT7 | Sirtuin 7 | Longevity |
| SOD2 | Superoxide dismutase 2, mitochondrial | Antioxidant |
| SPARC | Secreted protein, acidic, cysteine-rich (osteonectin) | Extra-cellular matrix – structure |
| SPTLC1 | Serine palmitoyltransferase, long chain base subunit 1 | Epidermal differentiation |
| TGFB1 | Transforming growth factor, beta 1 | Inflammation |

COSMETIC CARE METHOD BASED ON PHOTOACTIVE EXTRACTS OF MICROALGAE

CROSS-REFERENCE TO RELATED PATENT APPLICATIONS

This application is a U.S. National Stage Application under 35 U.S.C. § 371 of International Patent Application No. PCT/FR2020/000159 filed May 4, 2020, which claims the benefit of priority of French Patent Application No. 1904608 filed May 2, 2019, both of which are incorporated by reference in their entireties. The International Application was published on Nov. 5, 2020, as International Publication No. WO 2020/221971A1.

The present invention relates to a cosmetic care method for the skin comprising the steps of applying, to the skin, a composition comprising photoactive extracts of at least one microalga, and exposing the region to which said composition has been applied to light. The invention also comprises a lighting device for cosmetic care according to the method, and a kit comprising a cosmetic composition comprising photoactive extracts of at least one microalga and a lighting device according to the invention. The invention finally comprises the use of the device according to the invention for an anti-aging and/or anti-wrinkle treatment and/or a treatment promoting the healing of the skin region.

Nowadays, maintaining a youthful appearance is a constant concern. Over time, and in particular in the case of chronological and/or photo-induced aging, the skin undergoes a large number of changes and deteriorations which result, at the level of the tissues, in disruption of the architecture of the epidermis, of the dermo-epidermal junction, of the dermis, as well as of the blood supply and innervation systems, and slowing or dysfunction of various cellular metabolisms, such as those involved in the balance of the barrier function, or involved in melanogenesis. At the cellular level, the aging results in an alteration in the physiology or the metabolism of the main cell types, such as the fibroblasts of the dermis, keratinocytes of the epidermis, and also melanocytes.

The cutaneous aging results from two separate and independent processes which involve intrinsic and extrinsic factors. Intrinsic or chrono-biological aging corresponds to normal or physiological aging associated with age.

Intrinsic aging results in particular in slowing of the renewal of the cells of the epidermis, and the appearance of fine lines or wrinkles. At the level of the dermis, the biosynthesis of macromolecules such as collagen reduces with age, changing the mechanical properties of the dermis, resulting in cutaneous relaxation, which is one of the clinical signs of aging.

Extrinsic aging corresponds to aging which is caused, in a general manner, by the outside environment, and corresponds in particular to photoaging due to exposure to the sun. Photo-induced cutaneous aging, i.e. caused following exposure to the sun, is also referred to as photoaging or heliodermia. Photoaging is the result, at the level of the dermis, of the deterioration of collagen fibers, resulting in particular in clinical alterations such as thick wrinkles and the formation of a soft and weather-beaten skin. The aging of the skin is thus accelerated by chronic exposure to UV. Extrinsic aging can also be due to smoking, a diet too high in fat, or indeed to alcohol consumption. These elements influence in particular the gradual change of the redox environment towards a pro-oxidant state, and thus contribute to a progressive change in the endothelial factors leading to endothelial dysfunction.

There are thus a large number of cosmetic care methods referred to as "anti-aging," which are intended to prevent and/or treat aging, in particular photoaging, and the signs thereof, in particular to prevent the appearance of wrinkles, and to visibly reduce the wrinkles already present, but also to reduce or suppress age spots. These cosmetic care methods include, for example, the regular application of lotions or creams referred to as "anti-aging" or "anti-wrinkle," comprising various cosmetic active ingredients.

In a manner analogous to that of aging, in particular following an injury or surgery, the skin is made fragile, and the organism begins the process of healing, allowing the reconstruction of tissues. This process requires numerous cell types, and makes it possible to prevent hemorrhaging, to protect the organism, to clean the tissues to be reconstructed, and finally to close the wound.

A significant number of healing-promoting cosmetic care methods are available today, largely in the form of cream or lotion, and comprise various cosmetic active ingredients.

Among these anti-aging, anti-wrinkle and/or healing cosmetic active ingredients, microalgae appear as sources rich in lipids, proteins, polysaccharides, vitamins (B1, B6, B12, C, E, K, etc.), pigments and antioxidants, said pigments also having an antioxidant role. These include the carotenoids, the phycobiliproteins (phycoerythrin and phycocyanin), phycocyanin, phycoerythrin, astaxanthin, or indeed Beta-carotene.

Thus, various cosmetic compositions use extracts of microalgae as anti-aging and anti-wrinkle components. It is possible to cite in particular patent application CN 104224608, which describes an anti-aging and anti-wrinkle emulsion comprising extracts of *spirulina*, patent application US 2005/0220810, which describes an anti-aging and anti-wrinkle composition comprising extracts of *chlorella*, or indeed application JP 2007176832, which describes an anti-aging composition comprising extracts of *Aphanizomenon*.

In a similar manner, U.S. Pat. No. 7,285,266 can be cited, which describes a cosmetic composition comprising extracts of *Thalassiosira fluviatilis* or *Thalassiosira weissflogii*.

Of all their advantages, by virtue of their antioxidant properties these extracts of microalgae make it possible in particular to reduce the oxidative stress of the cells of the epidermis.

Contrary to the traditional antioxidant effects sought by a person skilled in the art in microalgae, as the main cosmetic active ingredient, the applicant has developed anti-aging and anti-wrinkle cosmetic compositions, and/or those that promote healing of the skin, comprising microalgae, the oxidant activity of which has been significantly increased by virtue of combining an application of light, allowing for the activation of the production of reactive oxygen derivatives (ROS).

Indeed, rather than capitalizing on the natural antioxidant properties of microalgae, the applicant has developed a method which makes it possible to activate the microalgae using light, which will thus increase the production, in the microalgae, of reactive oxygen derivatives (ROS), and increase the oxidation states of the cells of the epidermis, as well as cause an increase in the dependent dose of nitric oxide, allowing for an increase in the synthesis of collagen and a reduction in the release of pro-inflammatory cytokines and metalloproteinases.

The applicant has surprisingly been able to observe that the cellular activity thus stimulated will allow restoration of the skin and of wrinkles, and an increase in its elasticity, and, at the same time, the light activates the natural process of production of various constituents of the skin, and in particular the stimulation of the activity of fibroblasts, causing an increase in the production of collagen and fibers, and thus an anti-aging and anti-wrinkle effect that also promotes healing, cellular regeneration, and vascularization.

A first object of the invention is a cosmetic care method for a region of the skin, comprising the successive steps of:
- applying, to the skin region, a cosmetic composition comprising photoactive extracts of at least one microalga;
- exposing the skin region to which said composition has been applied to a light source emitting light at a wavelength of between 400 and 750 nm.

According to the invention, microalgae means a unicellular chlorophyllic photoautotroph. These include eukaryotic microalgae which are characterized by a cellular wall and a nucleus, comprising in particular chlorophytes, chrysophytes, pyrrophytes, coccolithophytes, diatoms, euglenophytes, rhodophytes, and trebouxiophytes, and procaryotes, also referred to as "cyanobacteria," having no nucleus or cell wall, and comprising the cyanophytes.

According to the invention, said at least one microalga is preferably photoactive.

Extracts or photoactive microalgae mean, according to the invention, extracts or microalgae which, upon exposure to light, preferably red light, trigger an oxidation reaction having an ROS production that is at least 50% greater than the production without exposure of said extracts to light, preferably an ROS production that is 100% greater, as well as an increase in the dependent dose of nitric oxide, allowing for an increase in the synthesis of collagen and a reduction in the release of pro-inflammatory cytokines and metalloproteinases. The term "photoreactive" can be used as an alternative to the term "photoactive" according to the present invention.

Light source means a device that emits light.

According to the invention, the extracts of microalgae preferably originate from *Tetraselmis suecica, Dunaliella salina, Rhodomonas salina, Rhodella maculata, Haematochococcus pluvialis, Porphyridium cruentum, Cyanophora paradoxa, Cylindrotheca closterium, Diacronema lutheri, Selenastrum capricornutum, Synechococus* sp., *Isochrysis* sp., *Tisochrysis lutea, Phaeodactylum tricornutum, Arthrospira platensis, Stichococcus bacillaris, Xanthonema* sp., *Nostoc* sp., *Pseudanabaena galeata, Chaetoceros calcitrans, Dunaliella Tertiolecta, Chlamydomonas reinhardtii, Tetraselmis tetrathele* and/or *Porphyridium purpureum*.

*Tetraselmis suecica* is a green halophilic microalga belonging to the class of the Chlorodendrophytes.

*Dunaliella salina* is a green halophilic microalga belonging to the class of the Chlorophytes, which develops spontaneously and preferably in very saline lagoon environments.

*Rhodomonas salina*, formerly *Pyrenomonas salina*, is an alga of the family of the cryptophytes, found in all aquatic environments, and used largely as a food for copepods.

*Rhodella maculata* or *Rhodella violacea* is a unicellular red alga of the Rhodellaceae family.

*Haematochococcus pluvialis* is a fresh water unicellular green alga of the Haematococcaceae family.

*Porphyridium cruentum* is a species of red algae of the Porphyridiophyceae family.

*Cyanophora paradoxa* is an alga of the Glaucocystaceae family.

*Cylindrotheca closterium* is a marine diatom living in intertidal environments.

*Diacronema lutheri* is a haptophyte used in aquaculture as food for marine invertebrates, and particularly for bivalves.

*Selenastrum capricornutum* or *Raphidocelis subcapitata* is a microalga commonly used as a bioindicator of the level of nutrients of toxic substances in fresh water, because it is very sensitive to the presence of toxic substances such as metals.

*Synechococus* sp. is a species of unicellular cyanobacteria living mainly in the marine environment.

*Isochrysis* sp. is a unicellular alga comprising a large quantity of fucoxanthin.

*Tisochrysis lutea* is a haptophyte which is frequently used as food in aquaculture.

*Phaeodactylum tricornutum* is a species of marine diatom cultivated in particular as food for mollusks and fish.

*Arthrospira platensis* is a species of the Phormidiaceae family.

*Stichococcus bacillaris* is a terrestrial alga which is found in particular on the ground, on stone walls, tiles, tree trunks, glass, wet banks.

*Xanthonema* sp. is a species of brown algae.

*Nostoc* sp., is a cyanobacterium of the Nostocaceae family.

*Dunaliella tertiolecta* is a green microalga that is capable, in some circumstances, of accumulating lipids.

*Pseudanabaena galeata* is a photosynthetic bacterium of the cyanophytes class.

*Chaetoceros calcitrans* is a species of diatom of the Chaetocerotaceae family.

*Chlamydomonas reinhardtii*, often referred to as green yeast, is a species of green algae.

*Tetraselmis tetrathele* is a green alga containing a significant quantity of antioxidants.

*Porphyridium purpureum*, also referred to as *porphyridium cruentum*, is a species of red algae of the Porphyridiophyceae family.

Particularly preferably, according to the invention, the extracts of microalgae are extracts of *Dunaliella salina*.

Particularly preferably, according to the invention, the extracts of microalgae are extracts of *Tetraselmis suecica*.

Particularly preferably, according to the invention, the extracts of microalgae are extracts of *Dunaliella salina* and *Tetraselmis suecica*.

According to the invention, the extracts are preferably microalgae liquid extracts, preferably obtained following culture of the microalgae, centrifugation, and grinding of the cake. These extracts may be hydrosoluble and/or liposoluble.

Even more preferably, according to the invention, these extracts are hydrosoluble.

According to the invention, said cosmetic composition comprising extracts of *Dunaliella salina* preferably comprises:
- between 0.0001% and 80% by weight of the composition of extracts of *Dunaliella salina*, preferably between 0.0001 and 50% by weight of the composition
- QSP 100 water
- 2.50% by weight of the composition of glycerin
- 0.40% by weight of the composition of triethanolamine
- 15% by weight of the composition of alcohol
- 1% by weight of the composition of coco caprylate caprate
- 1% by weight of the composition of isopropyl myristate 0.1% by weight of the composition of perfume According to the invention, said cosmetic composition comprising extracts of *Tetraselmis suecica* preferably comprises:
- between 0.0001% and 78% by weight of the composition of extracts of *Tetraselmis suecica*, preferably between 0.0001 and 50% by weight of the composition
- QSP 100 water
- 7.00% by weight of the composition of sweet almond oil
- 4.50% by weight of the composition of C12-15 alkyl benzoate
- 5.65% by weight of the composition of steareth
- 1.90% by weight of the composition of glyceryl stearate
- 1.40% by weight of the composition of dimethicone
- 0.25% by weight of the composition of carbomer
- 0.25% by weight of the composition of sodium benzoate
- 0.20% by weight of the composition of perfume
- 0.18% by weight of the composition of sodium benzoate
- 0.10% by weight of the composition of EDTA According to the invention, said cosmetic composition comprising extracts of *Dunaliella salina* and of *Tetraselmis suecica* preferably comprises:
- between 0.0001% and 76% by weight of the composition of extracts of *Tetraselmis suecica*, preferably between 0.0001 and 50% by weight of the composition
- between 0.0001% and 76% by weight of the composition of extracts of *Dunaliella salina*, preferably between 0.0001 and 50% by weight of the composition
- QSP 100 water
- 4.00% by weight of the composition of cottonseed oil
- 3.2% by weight of the composition of glycerin
- 4.00% by weight of the composition of sunflower oil
- 3.00% by weight of the composition of octyldodecanol
- 3.70% by weight of the composition of propanediol
- 1.5% by weight of the composition of sodium acrylates copolymer
- 1.10% by weight of the composition of caprylic/capric triglyceride
- 0.8% by weight of the composition of pentylene glycol
- 0.8% by weight of the composition of aluminum starch octenylsuccinate
- 0.70% by weight of the composition of benzyl alcohol
- 0.50% by weight of the composition of lecithin
- 0.20% by weight of the composition of coco-caprylate/caprate
- 0.20% by weight of the composition of tocopherol
- 0.08% by weight of the composition of EDTA
- 0.06% by weight of the composition of dehydroacetic acid According to the invention, said light is preferably red light having a wavelength of between 625 and 670 nm, preferably 645 nm, and an intensity of from 140 to 180 $\mu mol \cdot s^{-1} \cdot m^{-2}$ photons, preferably 155 to 170 $\mu mol \cdot s^{-1} \cdot m^{-2}$ photons.

According to the invention, the exposure to the light is preferably achieved using electroluminescent diodes, laser, and/or intense pulsed light.

Intense pulse light or IPL, also referred to as flash lamp, is understood, according to the invention, as a technology comprising polychromatic lamps having a high-intensity discharge and which are filled with a rare gas, for example xenon. They function by converting the stored electrical energy into intense bursts of radiant energy. The emitted light covers the light spectral regions of ultraviolet, visible and infrared, i.e. from 350 nm to 1200 nm, including red light of a wavelength of from 625 to 670 nm, preferably 645 nm.

Electroluminescent diode means, according to the invention, electronic components which, when an electrical current passes therethrough, emit low-frequency light. It emits a light which is considered "cold" because it does not produce heat. The electroluminescent diodes emit light in a spectrum which extends from visible to infrared.

According to the invention, said electroluminescent diode preferably emits red light having a wavelength of from 625 to 670 nm, preferably 645 nm.

According to the preceding claims, the time of exposure to the light is preferably from 1 second to 60 minutes, preferably from 30 seconds to 40 minutes, even more preferably from 10 to 20 minutes.

Time of exposure to the light means, according to the invention, the time during which the skin of the individual is exposed to the light.

According to the invention, the light source is preferably placed at a distance of from 2 mm to 10 cm from the skin region to be treated.

According to the invention, the light source preferably provides light at an intensity of between 3 and 150 $J/cm^2$.

According to a second aspect, the invention relates to a lighting device for cosmetic care according to the method according to the invention, said device consisting of a housing comprising a light source, said light source emitting light in a spectrum of wavelengths of between 400 and 750 nm, preferably between 625 and 670 nm, and an intensity of from 140 to 180 $\mu mol \cdot s^{-1} \cdot m^{-2}$ photons, preferably between 155 and 170 $\mu mol \cdot s^{-1} \cdot m^{-2}$ photons.

According to the invention, said light source preferably emits light at a wavelength of 645 nm.

According to the invention, said light source preferably comprises at least one LED which emits light in a spectrum of wavelengths of between 400 and 750 nm, preferably between 625 and 670 nm, and an intensity of from 140 to 180 $\mu mol \cdot s^{-1} \cdot m^{-2}$ photons, preferably between 155 and 170 $\mu mol \cdot s^{-1} \cdot m^{-2}$ photons.

According to the invention, said at least one LED preferably emits light at a wavelength of 645 nm.

According to the invention, the light source preferably represents a surface area of from 0.15 $cm^2$ to 2900 $cm^2$.

According to an embodiment of the invention, the light source preferably represents a surface area of from 0.25 to 1450 $cm^2$.

According to the invention, said device preferably takes the form of a mask, a panel, or a manual apparatus.

Mask means, according to the invention, a device that is capable of exposing all or some of a face to the light. The light source could represent a surface area of approximately the surface area of a face, i.e. approximately 500 $cm^2$.

Apparatus for manual use means, according to the invention, a handheld device which makes it possible to expose the skin of an individual in a localized manner. An example of a manual apparatus may be a pen, and the light source could then represent a surface area of approximately 0.15 to 2 $cm^2$, or a device of the size of an electric razor, and the light source could then represent a surface area of approximately 2 to 7 $cm^2$.

Panel means, according to the invention, a device that is capable of exposing a very large part of an individual's body to the light. This type of device can even go so far as to expose an individual's entire body. The light source could then represent a surface area of from 550 $cm^2$ to over 1500 $cm^2$.

According to a third aspect, the invention relates to a kit comprising:

a cosmetic composition comprising photoactive extracts of at least one microalga;

a lighting device for cosmetic care according to the invention.

According to the invention, the extracts of microalgae are preferably selected from extracts of *Tetraselmis suecica*, *Dunaliella salina*, *Rhodomonas salina*, *Rhodella maculata*, *Haematochococcus pluvialis*, *Porphyridium cruentum*, *Cyanophora paradoxa*, *Cylindrotheca closterium*, *Diacronema lutheri*, *Selenastrum capricornutum*, *Synechococus* sp., *Isochrysis* sp., *Tisochrysis lutea*, *Phaeodactylum tricornutum*, *Arthrospira platensis*, *Stichococcus bacillaris*, *Xanthonema* sp., *Nostoc* sp., *Pseudanabaena galeata*, *Chaetoceros calcitrans*, *Dunaliella Tertiolecta*, *Chlamydomonas reinhardtii*, *Tetraselmis tetrathele* and/or *Porphyridium purpureum*.

According to the invention, said composition preferably comprises extracts of *Tetraselmis suecica*.

According to the invention, said composition preferably comprises extracts of *Dunaliella salina*.

According to the invention, said lighting device preferably emits light at a wavelength of between 400 and 750 nm, and an intensity of from 140 to 180 $\mu mol \cdot s^{-1} \cdot m^{-2}$ photons, preferably between 155 and 170 $\mu mol \cdot s^{-1} \cdot m^{-2}$ photons.

According to the invention, said light is preferably red light having a wavelength of between 625 and 670 nm, preferably 645 nm.

According to a fourth aspect, the invention relates to the use of the device according to the invention for an anti-aging and/or anti-wrinkle treatment and/or a treatment promoting the healing of the skin region.

FIGURES

FIG. 1: Production of ROS following light exposure (645 nm) for 25 minutes (in gray) for a plurality of photoactive extracts of microalgae, at a dilution factor of 500. The results when the extracts are kept in the dark are shown in black.

Figure 2:
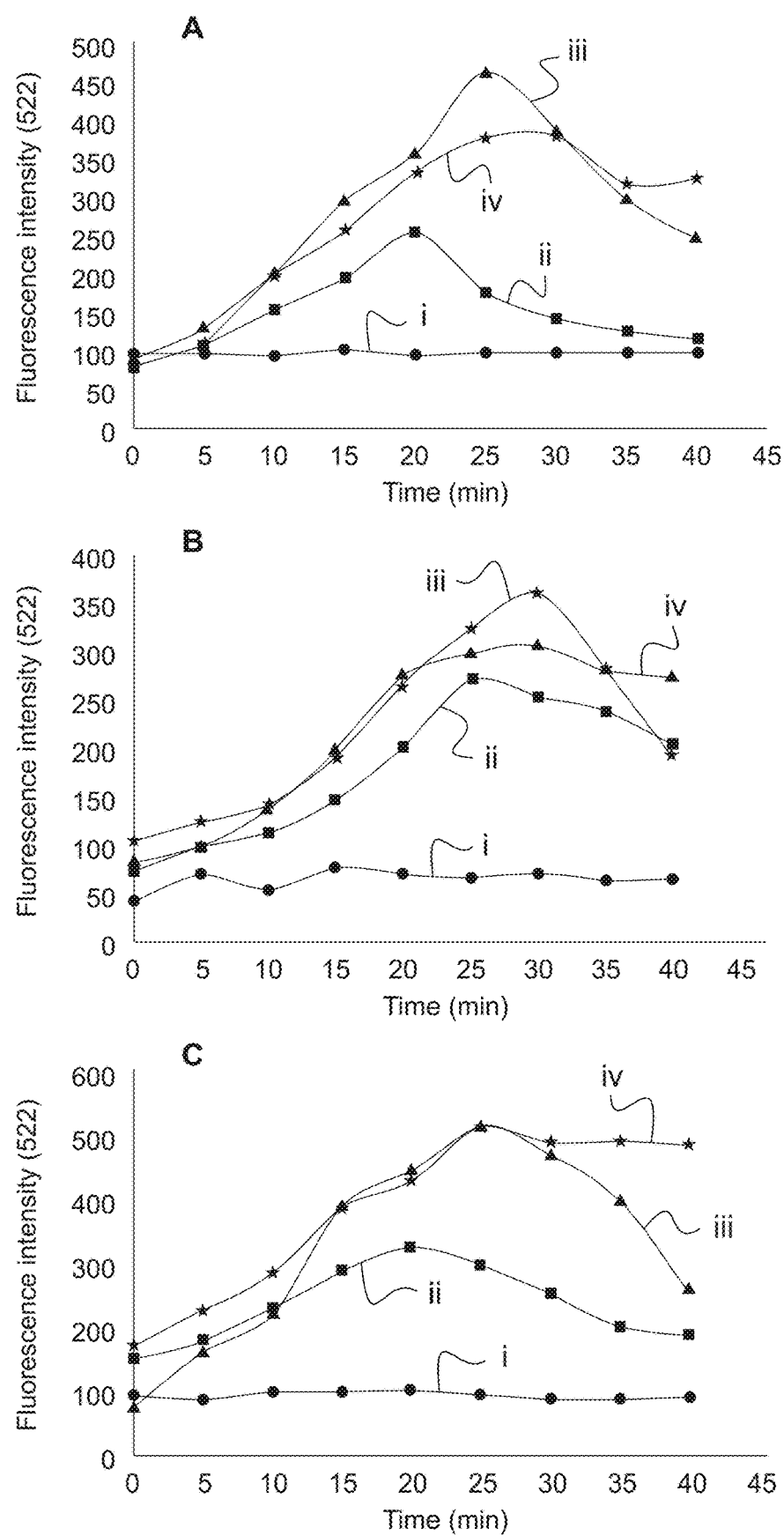

FIG. 2: Influence of the exposure duration on the production of oxidative molecules (ROS), depending on the extracts. The extracts originating from *Dunaliella salina* (DS) (FIG. 2A), *Tetraselmis suecica* (TS) (FIG. 2B), and *Rhodomonas salina* (RS) (FIG. 2C), are kept in the dark (i), or exposed for 1 minute (ii), 10 minutes (iii) or continuously (iv), to light exposure at 645 nm.

FIGS. 3A-3B: Genes evaluated during the study of the effectiveness on the expression of the mRNA of cells of the skin by microfluidic RT-qPCR.

Figure 4:
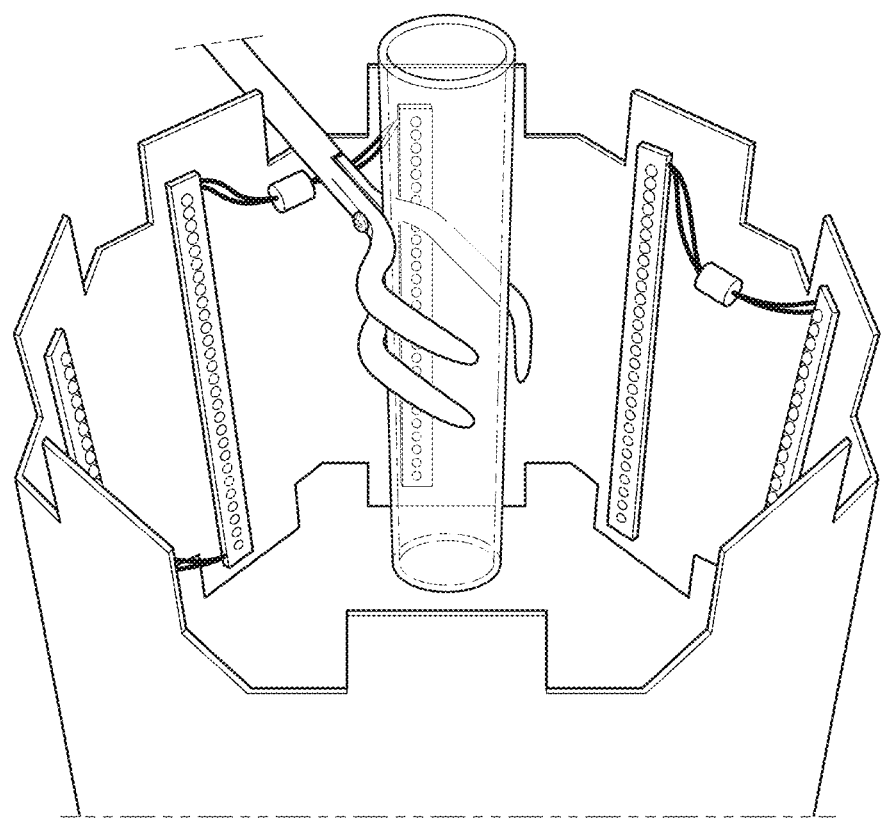

FIG. 4: Red LED module (wavelength=645 nm) preset to 160 $\mu mol/m^2/s$ used for photoactivation (Example 5).

EXAMPLES

Example 1: Preparation of Samples

Characterization of the production of oxidative molecules in the extracts of microalgae:

The extracts of the algae *Dunaliella salina* (DS), *Dunaliella tertiolecta* (TD), *Tetraselmis suecica* (TS), *Chlamydomonas reinhardtii* (CR), *Haematococcus pluvialis* (HP), *Tetraselmis tetrathele* (TT), *Rhodomonas salina* (RS), *Porphyridium purpureum* (PP), *Rhodella maculata* (RM) are selected to characterize the increase in the production of oxidative molecules when they are stimulated with light.

In order to achieve this, the algae are placed in 200 ml cultures. After a cell count at a wavelength of 680 nm, 100 to 150 ml of the solution containing the algae are then centrifuged for 10 minutes at 12,000 rpm.

The cake is then ground, and the ground material is adjusted to $5.0.10^5$ cells/ml in 150 ml PBS.

After a cell count at a wavelength of 680 nm, this adjusted ground material is then centrifuged for 10 minutes at 12,000 rpm.

Finally, the supernatant is filtered at 0.2 µm in order to obtain the sample ready to be analyzed.

Once ready for analysis, the samples made up of extracts of these algae are placed:

1. In the dark, and 15 µl of the reaction medium are added to 30 ml of supernatant filtered at 0.2 µm;
2. In the dark, and 15 µl of the reaction medium are added to 30 ml of supernatant filtered at 0.2 µm, followed by continuous exposure to light at 645 nm, at an intensity of 166 $\mu mol \cdot s^{-1} \cdot m^{-2}$.
3. In the dark, and 30 ml of supernatant filtered at 0.2 µm are exposed to bubbling with dinitrogen for 30 minutes, and then mixed with 15 µl of reaction medium. A step of light exposure is then carried out, at 645 nm, at an intensity of 166 $\mu mol \cdot s^{-1} \cdot m^{-2}$.

Example 2: Screening of Strains

The various extracts are then studied, keeping them in the dark or exposing them for 25 minutes to light exposure of 645 nm, at a dilution factor of 500, by means of fluorescence analyses performed using a spectrofluorometer. The parameters are as follows:

Ex: 500 Em: 522
Ex. scanning range 495-505
Em. scanning range 400-650

The results are shown in FIG. 1.

These results show an increase in the production of ROS after light exposure, for all the extracts studied.

In detail, the production of ROS is 5 times greater for the extracts of DS, 5.5 times greater for the extracts of TD, 3.6 times greater for the extracts of TS, 2.1 times for the extracts of CR, 2 times for the extracts of PP, 6.8 times for the extracts of RS, 2.3 times for the extracts of RM, 3.1 times for the extracts of HP, and 3.4 times for the extracts of TT.

Example 3: Influence of the Exposure Duration

The extracts are then studied on the basis of the exposure duration. The 4 stages studied are:

Extracts kept in the dark
Extracts having 1 minute of light exposure at 645 nm
Extracts having 10 minutes of light exposure at 645 nm
Extracts continuously exposed to light exposure at 645 nm The results for DS (FIG. 2A), TS (FIG. 2B), and RS (FIG. 2C) are shown in FIG. 2.

These results show a constant ROS production in the dark, whatever the extract of microalgae.

For the exposure at 1 minute, the extracts of DS, TS and RS reveal an increase in the production of ROS which wears off after approximately 20/25 minutes. The production increases, to reach a maximum at around 20/25 minutes, and then drops. Thus, at most an increase of approximately 2.5 times is observed for DS, of 5 times for TS, and of approximately 3 time for RS.

Following exposure for 10 minutes, the extracts of DS, TS and RS exhibit an increase in the production of ROS which is greater than that characteristic after exposure at 1 minute. The production increases, to reach a maximum at around 25/30 minutes, and then drops. Thus, at most an increase of approximately 4.5 times is observed for DS, of 7 times for TS, and of 5 time for RS, compared with the lack of exposure.

In the case of continuous exposure, it is observed that the curves are close to those after exposure of 10 minutes. The production thus increases, to obtain a maximum at around 25/30 minutes, and then drops. For DS, a maximum production is observed after 25 minutes, of 3.5 times greater than that in the dark, thus being slightly less than the exposure for 10 minutes. During the first 25 minutes, the progressive increase in the production of ROS is similar to that characteristic for exposure at 10 minutes. However, after 35 minutes, the continuous exposure appears to exhibit a greater production of ROS than that following exposure at 10 minutes. For TS, a maximum production is observed after 30 minutes, of 6 times greater than that in the dark, thus being slightly less than the exposure for 10 minutes. For the first 25 minutes, the progressive increase in the production of ROS is similar to that characteristic of exposure at 10 minutes. However, after 35 minutes, the continuous exposure appears to exhibit a greater production of ROS than that following exposure at 10 minutes. Regarding RS, a maximum production is observed after 25 minutes, of 5 times greater than that in the dark, thus being identical to the exposure for 10 minutes. However, after 35 minutes, the continuous exposure appears to exhibit a lasting production of ROS that is greater than that following exposure at 10 minutes.

In conclusion, there is no continuous increase in the response, resulting in reaching a specific plateau at each strain of the maximum production of ROS, achieved around 25/30 minutes, and for an exposure rate of 10 minutes. Moreover, it can clearly be seen that the termination of the production is dependent on the exposure duration, the exposures at 1 and 10 minutes showing a decrease in the production of ROS after 20 to 30 minutes.

Example 4: Clinical Evaluation on 30 Subjects of Anti-Aging Cosmetic Care Using a Device that Emits Light at a Wavelength of 645 nm The clinical study relates, overall, to 30 women aged between 35 and 70 years.
a) Performing the session of applying the cosmetic composition, and applying light at 645 nm.

A clinical dermatological examination of the tone of the skin (analysis by touch) and of the lines or wrinkles is carried out (semi-quantitative scores). Macrophotographs (subject without makeup, standard poses) are taken. Measurements of the surface area of the wrinkles, their depth, and the roughness of the skin are taken at D0 and D28, using a measuring apparatus (Skin Station).

Application of 0.4 g of composition to the face.

Exposure of the skin region containing the crow's feet to a lighting device emitting light at a wavelength of between 625 and 670 nm.

Application of the light source at 645 nm (duration, distance, intensity).
c) Conclusion A clinical improvement is observed, following care using the composition and the device, in 27 of the 30 subjects.

The product is extremely well tolerated, and the cosmetic assessment is, overall, very good.

The cosmetic care method according to the invention thus makes it possible to significantly reduce the wrinkles of the skin.

Example 5: Evaluation of the Effectiveness on the Expression of the mRNA of Cells of the Skin by Microfluidic RT-qPCR Following Activation of the Extracts Using Light The entirety of this handling is carried out in semi-darkness.
Material:
  module of red LEDs (wavelength=645 nm) preset to 160 µmol/m$^2$/s, shown in FIG. 4.
  20 ml glass test tube
  clamp
  support comprising a rod
Protocol:
  In the semi-darkness, 5 ml of extract are poured into the test tube.

The test tube is then placed in the center of the module of LEDs by being fixed to the rod of the support by virtue of the clamp.

The module of red LEDs is then illuminated, and the light is left to act for 10 minutes.

After this 10 minutes, the light is cut and the sample remains in the semi-darkness.

The extract contained in the tube is withdrawn using a pipette, without stirring.

The photoactivated extract is used fresh, in the remainder of the protocol.

The experiment is performed three times (n=3) on normal human epidermal keratinocytes (NHEK) and normal human dermal fibroblasts (NHDF), where the extracts activated as described above are used.
Analysis Method:

The mRNA are extracted and reverse-transcribed into cDNA. The gene expression is quantified using qPCR, and normalized by the expression of reference genes. In order to confirm an activator or inhibitor effect, the values are compared with the reference condition, after contacting with the extracts.

The genes evaluated are indicated in FIGS. 3A-3B.

An increase in the expression of the genes Claudine 1, Collagen, Fibrillin 1 and 2 is observed, as well as, in a general manner, antioxidant genes. At the same time, a reduction in the expression of metallopeptidase 1, 3 and 9 genes, and inflammation, is observed.

In conclusion, a reduction in the expression of genes promoting cutaneous aging is observed.

The invention claimed is:

1. A cosmetic care method for a region of the skin, comprising the successive steps of:
    applying, to the skin region, a cosmetic composition comprising an effective amount of a photoactive extract of Tetraselmis Suecica; and
    exposing the skin region for a duration of time to a light source emitting red light at a wavelength of between 625 and 670 nm, and an intensity of from 140 to 180 µmol·s$^{31\ 1}$·m$^{-2}$ photons, thereby triggering an oxidation reaction having activation of a production of reactive oxygen derivatives (ROS) that is greater than the production of ROS without exposure of the photoactive extracts of *Tetraselmis Suecica* to the red light.

2. Cosmetic care method according to claim 1, characterized in that said red light has a wavelength of 645 nm, and an intensity of from 155 to 170 µmol·s$^{31\ 1}$·m$^{-2}$ photons.

3. Cosmetic care method according to claim 1, characterized in that the exposure to the red light is achieved using electroluminescent diodes, laser, and/or intense pulsed light.

4. Cosmetic care method according to claim 1, characterized in that the time of exposure to the red light is from 30 seconds to 40minutes.

\* \* \* \* \*